United States Patent [19]

McIntyre et al.

[11] Patent Number: 4,479,868
[45] Date of Patent: Oct. 30, 1984

[54] GAS MEASURING PROBE

[75] Inventors: William H. McIntyre, Orrville, Ohio; Sai-Kwing Lau, Verona; Subhash C. Singhal, Murrysville, both of Pa.

[73] Assignee: Westinghouse Electric Corp., Pittsburgh, Pa.

[21] Appl. No.: 544,159

[22] Filed: Oct. 21, 1983

[51] Int. Cl.³ .............................................. G01N 27/58
[52] U.S. Cl. ................................. 204/426; 204/427; 204/424
[58] Field of Search ............... 204/421, 424, 425, 426, 204/427

[56] References Cited

U.S. PATENT DOCUMENTS

| | | | |
|---|---|---|---|
| 3,454,486 | 7/1969 | Davies | 204/427 |
| 3,791,954 | 2/1974 | Makoto Noda et al. | 204/427 X |
| 3,808,639 | 5/1974 | Faurchou et al. | 204/427 X |
| 3,819,500 | 6/1974 | Van Esdonk et al. | 204/426 |
| 3,928,161 | 12/1975 | McIntyre et al. | 204/406 X |
| 4,284,487 | 8/1981 | Barnes et al. | 204/408 |

Primary Examiner—G. L. Kaplan
Assistant Examiner—Nam X. Nguyen
Attorney, Agent, or Firm—T. R. Trempus

[57] ABSTRACT

The invention provides both preferred material alloys and electrode lead wire configurations for electrically connecting the solid electrolyte cell in a gas sensing probe to a remote measuring circuit.

16 Claims, 7 Drawing Figures

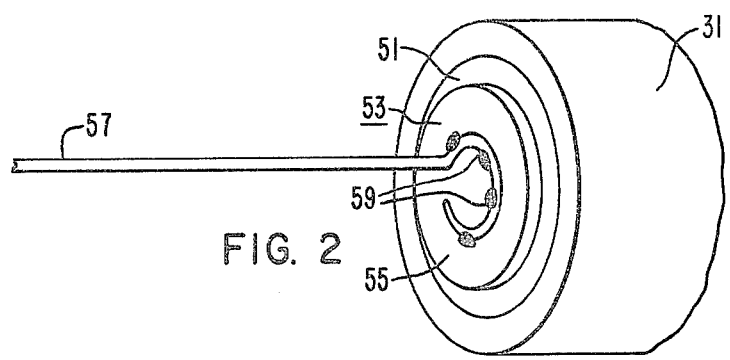
FIG. 2
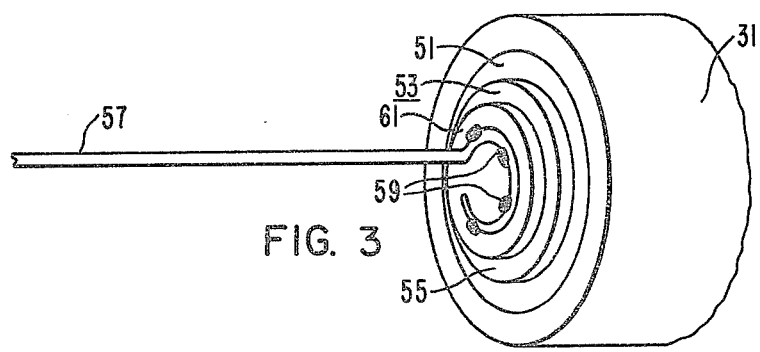
FIG. 3
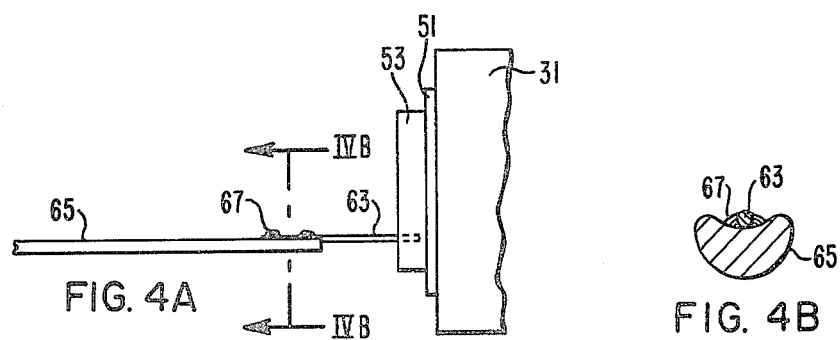
FIG. 4A
FIG. 4B
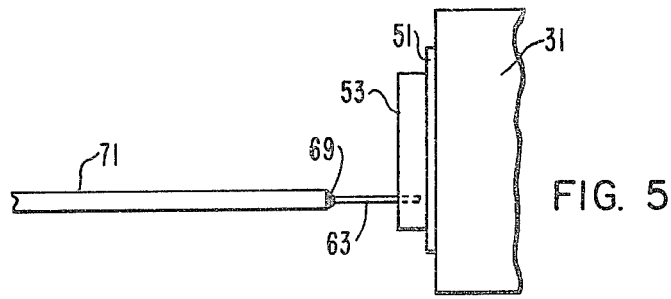
FIG. 5

4,479,868

GAS MEASURING PROBE

FIELD OF THE INVENTION

The invention relates generally to gas measuring probes, particularly such probes as are used in industrial applications. The invention is specifically directed to materials and designs for electrode lead wires in solid electrolyte sensors.

BACKGROUND OF THE INVENTION

Solid electrolyte oxygen sensors are widely used for monitoring high temperature combustion systems in order to maximize combustion efficiency. The major components of these sensors include a stabilized zirconia electrolyte cell which is connected to electronic measuring equipment by long lengths of lead wires. The material currently used for these lead wires is almost exclusively platinum. It has therefore been a long sought after goal in the art of oxygen analyzers to minimize the use of platinum or other noble metal leads since such materials are relatively expensive and platinum itself is considered a strategic material to the United States.

In order to minimize the use of platinum in its oxygen probes, Westinghouse Electric Corporation, in its model 218 probe, grounds the platinum lead from one surface of the solid electrolyte cell surface to a stainless steel mounting bracket which supports the electrolyte cell. The stainless steel mounting bracket is in turn grounded through intermediate members to the furnace wall. With this mechanical configuration, the use of platinum is effectively reduced since only one, rather than two platinum leads are required to pass from the electrolyte cell to the electrical measurement circuitry which is also grounded to the furnace wall. The existence of various junctions between dissimilar metals in the ground path of this design, however, can generate thermoelectric differences in the output of solid electrolyte cell and electrical compensation is required.

In another effort to minimize the use of platinum wire and to allegedly facilitate on-site servicing of an oxygen probe, U.S. Pat. No. 4,284,487, assigned to the Milton Roy Company, teaches a probe design in which the platinum lead wires are connected by nickel alloy screws and crimps to nickel alloy rod terminals situated in the hot combustion zone. Since all of the aforementioned electrical connections are made at approximately the same temperature, the likelihood of unbalanced thermocouples is minimized. In order to remove the connectors for the servicing of the probe, the other ends of the nickel alloy rod terminals are formed into the prongs of a male-type plug connector that mates with a female-type plug for disassembly. While the use of the design taught by the aforesaid patent can reduce the use of platinum, there are several potential problems. At the typical cell operating temperature of 1550° F. (843° C.) these nickel alloy parts are susceptible to rapid oxidation and the oxide scales formed on the nickel alloy screw, crimp and terminals surfaces can act as insulating surfaces and render the several connectors electrically discontinuous. More particularly, such oxidation occurs at temperatures higher than about 1000° F. (538° C.). Moreover, the nickel-alloy-platinum interfaces as well as the nickel alloy parts in contact with each other can easily fuse together at the high operating temperature via solid-state diffusion and become nondetachable. For these reasons the application of the referenced design is primarily limited to temperatures below 1000° F. (538° C.). It is thus inadequate for many industrial applications where temperatures as high as 1600° F. (868° C.) are commonly encountered.

It is therefore an object of this invention to replace, in one embodiment of the invention, all of the platinum lead wires extending from the zirconia electrolyte cell, and in an alternative embodiment, to eliminate a substantial portion of the platinum lead wires.

It is a further object of the present invention to provide a design for lead wires in an oxygen probe that will provide the desired satisfactory operating characteristics of all the replaced platinum lead wires at the cell operating temperature of 1550° F. (843° C.).

It is yet another object of the present invention to lower the cost of such high temperature oxygen probes by eliminating all or substantially all of the platinum lead wires which are utilized therein.

SUMMARY OF THE INVENTION

The invention provides materials and design configurations for the electrode lead wires which extend between the solid electrolyte cell and a remote measuring circuit in a high temperature gas sensing probe. The invention provides for the welded connection, in one embodiment, of an alloy wire to a platinum gauze pad mounted on a sintered electrode on the solid electrolyte. In a second embodiment, a platinum disc is disposed between the gauze pad and the alloy lead wire. A third embodiment mounts a platinum lead wire in the gauze pad on the sintered electrode and butt welds an alloy lead wire to the extension wire in an end-to-end relationship. In a forth embodiment, an alloy lead wire is semicircular in cross section at one end and the platinum extension wire is welded to the seatlike area defined by the shape of the alloy lead wire.

The alloy is selected from the group consisting of Chromel A (79 Ni-20 Cr-1 Si) and Inconel 600 (77 Ni-15.8 Cr-7.2 Fe). All compositions are in weight percent. Chromel A is a registered trademark of the Hoskins Manufacturing Company and Inconel 600 is a registered trademark of the International Nickel Company, Inc.

BRIEF DESCRIPTION OF THE DRAWINGS

The above as well as other features and advantages of the present invention will become apparent through consideration of the detailed description in connection with the accompanying drawings in which:

FIG. 2 is a detail of one embodiment of this invention, utilizing an alloy/platinum gauze weld design;

FIG. 3 is a detail of a further embodiment of the present invention utilizing an alloy/platinum disc weld design;

FIG. 4A is a detail of another embodiment of the invention illustrating an alloy/platinum extension lead lap joint design;

FIG. 4B is a cross section of the embodiment of FIG. 4A along lines IV—IV thereof; and FIG. 5 is a detail of an additional embodiment of this invention illustrating an alloy/platinum extension lead butt joint design.

DESCRIPTION OF THE PREFERRED EMBODIMENT

The invention provides materials and design configurations for electrode lead wires in solid electrolyte sensors. The combination of specific electrode lead wire materials and their design configurations substantially eliminate the aforedescribed drawbacks found in gas sensor probes, i.e., unbalanced thermocouples and the rapid oxidation which tends to create insulating layers of oxide scales which can render connectors electrically discontinuous.

Figure 1A:
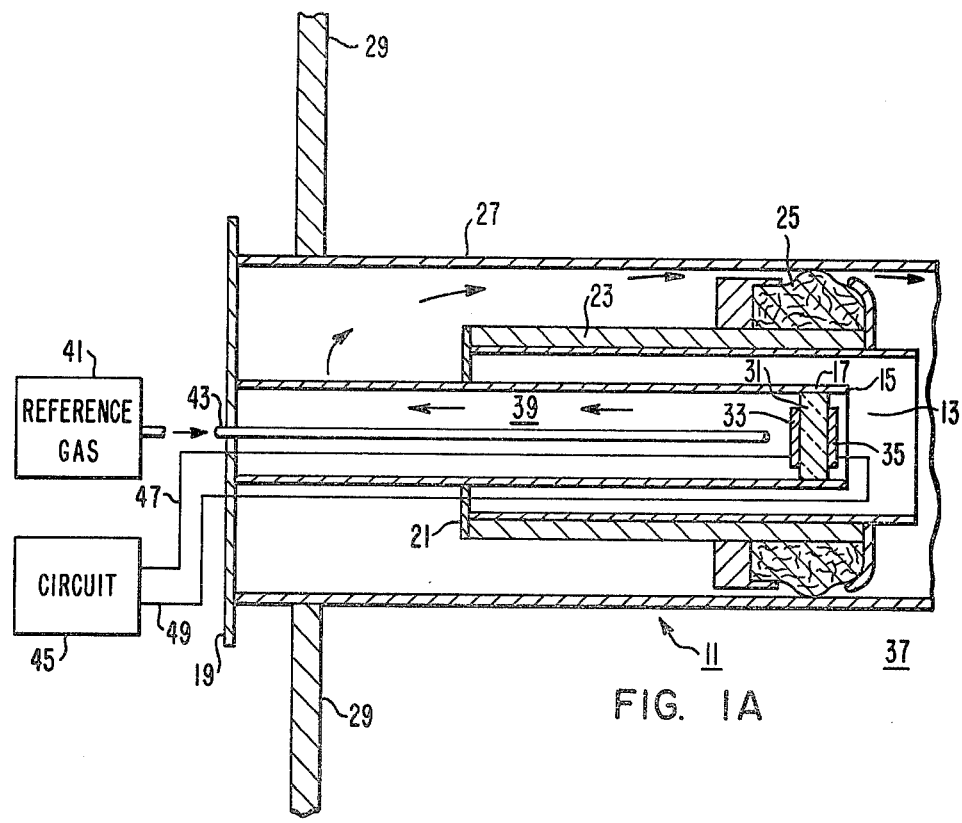
FIGS. 1A and 1B are schematic illustrations of typical solid electrolyte probe assemblies incorporating the materials and designs for electrode lead wires according to the teachings of the present invention.
Figure 1B:
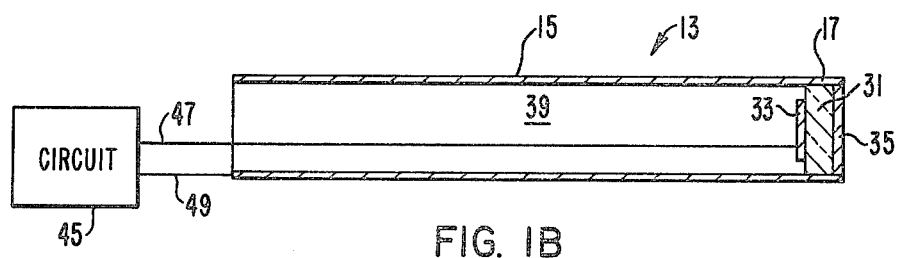

Turning to FIGS. 1A and 1B, an industrial-type solid electrolyte gas analyzer probe is generally indicated by the reference character 11 and like reference characters represent generally equivalent components. FIG. 1B illustrates an alternate method of providing electrical continuity between a sensor cell and the measuring circuitry as will be described below. While the analyzer probe assembly 11 illustrated is for the in-situ measurement of the gas constituent of a process gas environment, it is to be understood that a gas analyzer can be of the type mounted outside of the process gas environment with the gas constituent drawn through a sample tube. The gas analyzer probe 11 is but an exemplar, and is not to be construed as a limitation to the application of the present invention.

The gas analyzer probe 11 includes a disc-shaped solid electrolyte electrochemical connection cell 13 sealed with a support tube 15 via a seal 17. The support tube 15, which may typically be a metal member, passes through a first bulkhead member 19 and a second bulkhead member 21. The second bulkhead member 21 includes a tubular member 23 which supports an annular porous dust seal 25 which contacts an outer tubular shell member 27 extending from the first bulkhead 19. The outer tubular shell member 27 is secured within an opening of the wall 29 of the process gas enclosure which may typically be a stack in an industrial environment. The solid electrolyte electrochemical cell 13 consists of an ion-conductive solid electrolyte element 31 having a reference electrode 33 and a sensing electrode 35 disposed on opposite surfaces thereof. The composition of the solid electrolyte member 31 is selected so as to render the cell 13 responsive to a particular gas constituent of interest in the process, or monitored gas, gas environment 37. The gas constituent of interest may be oxygen, a combustibles constituent, a pollutant constituent, etc. A known or stable reference gas environment 39 is maintained in contact with the reference electrode 33 by flowing reference gas at a controlled rate from a remote reference gas source 41 through an inlet tube member 43. The electrical signal developed by the electrochemical cell 13 in response to the partial pressure of the gas constituent of interest of the process gas environment 37 is monitored by a remote measuring circuit 45 connected to the electrodes 33 and 35 via electrical leads 47 and 49. It is, of course, possible to modify the above-described gas analyzer probe 11 in order to incorporate additional features. The present invention, however, is directed to a particular aspect of the probe design and operation, that is, the lead wires 47 and 49 and the manner in which they are connected to electrodes 33 and 35 and the materials from which they are manufactured.

Again, for illustrative purposes, the solid electrolyte electrochemical cell 31 is shown as a disclike member, it is to be appreciated that the electrochemical cell may also be configured in the shape of a cylindrical or tube-like member in which one side of the tube is in contact with the process gas and the other side is in contact with the reference gas. The gas analyzer 11 of FIG. 1A also demonstrates that the lead wires 47 and 49 are of substantial length and the cost of providing such lengths of platinum wire is obvious. Even when one of the leads is grounded to the metal support tube 15 as in FIG. 1B, a substantial length of platinum wire is still required. The designs, which will be described in detail below in connection with the remaining figures, not only substantially reduce the use of platinum, they also eliminate much of the unbalanced thermoelectric differences in the sensor cell output. More importantly, since the joints in the designs according to this invention are welded, instead of the prior art teachings of mechanical electrical connections, electrical continuity at the electrode-lead wire interface is not effected by surface oxidation. As a result, the present lead wire design permits probe use at temperatures in excess of 1000° F. (538° C.). In addition, due to the low cost of the alloy wires utilized by the present invention, the lead wire can actually be considered disposable, thus eliminating the need for high temperature alloy screws, crimps, and rods with male-type connectors as employed by presently available gas analyzer probes.

The several embodiments illustrated in FIGS. 2 through 5 replace either all or substantially all of the platinum lead wire with a wire material formed from an alloy composition. The proposed alloy material is characterized by a resistance to oxidation which enables the material to withstand the expected temperature and environmental conditions encountered by the platinum wire in gas analyzer probes. Additionally, since contact between platinum and the alloy material is inevitably encountered in the design of the present invention, the alloy material should minimize diffusion instability problems which typically result from the contacting of platinum with a dissimilar material.

A detailed study of the oxidation resistance of various alloy materials determined that certain iron base and nickel base high temperature alloys possess the required oxidation resistance to withstand the expected temperature and environmental conditions encountered by the original platinum wire in gas probes. Moreover, because, as will be described below, there is contact between platinum and the alloy material, the potential problem of diffusional instability had to be considered. Rapid interdiffusion at the platinum-alloy material junction could lead to serious performance problems including loss of electrical continuity, loss of oxidation resistance due to a deleterious change in local alloy composition, or even actual physical separation due to the Kirdendall void formation. It was therefore necessary to examine the diffusional behavior of each alloy in addition to the alloy's oxidation behavior.

While several alloys were considered, two alloys were found to have the aforedescribed, desired characteristics. Platinum-alloy material diffusion couples with intimate interfacial contacts were prepared and diffusionheat treated at two temperatures, 1550° F. (843° C.), the expected gas analyzer probe operating temperature and 2100° F. (1149° C.) for accelerated testing. The two preferred alloy materials are Chromel A and Inconel 600.

Chromel A consists of nickel, 79 weight percent, chromium 20 weight percent, and silicon approximately 1 weight percent. The alloy Chromel A demonstrated good diffusional stability with platinum at the 1550° F. (843° C.) diffusion temperature test. Neither Kirdendall voids nor intermetallic compound formation was observed. Even during the 2100° F. (1149° C.) diffusion temperature test, it was found that the use of the end-to-end butt joint, as will be described below, could provide long term structural stability.

Inconel 600, consisting of nickel, 77 weight percent, chromium, 15.8 weight percent and iron, 7.2 weight percent, exhibited excellent diffusional stability.

However, besides diffusional stability, resistance to oxidation attack is an equally important requirement. Since the composition in the diffusion affected zone is different from the alloy itself, the oxidation resistance at the alloy-platinum joints could be far different from that of the alloy. This synergistic diffusion-oxidation effect on the overall stability of these two candidate wire materials was, therefore, also evaluated. Three types of specimens were prepared for testing: (1) the alloy wire spot welded to a platinum wire gauze electrode pad, (2) the alloy wire spot welded to a platinum wire via a lap joint, and (3) the alloy wire joined end-to-end with a platinum wire (butt joint) by the percussion weld technique. These specimens were oxidized in air at 1550° F. and 2100° F. for times ranging from 25 to 880 hours. To achieve more severe testing conditions, thermal cycling between furnace and room temperatures was used in some tests. All the specimens survived these severe tests without failure at the joints. It has been concluded that both Chromel A and Inconel 600 when used in the design applications of the present invention successfully eliminate the need for extensive platinum wire use or unstable mechanical connections in the gas analyzer probe.

Throughout the remaining figures, it will be appreciated that while only a single electrode connection is illustrated and specifically described, the technique of this invention is equally applicable to both the reference electrode 33 and the sensing electrode 35 which are shown in FIG. 1. The several embodiments of the electrode lead wire configuration of the invention are shown in FIGS. 2 through 5.

Turning now to FIG. 2, an isometric sectional view of an ion-conductive solid electrolyte element 31 illustrates an alloy/platinum gauze weld design. The electrolyte element 31 has a sintered electrode 51 thereon adapted to partially receive a platinum gauze pad 53. The gauze pad 53 is typically one square inch (2.5 cm$^2$) and formed through an over and under weaving technique to consist of a very fine woven member. The gauze pad 53 is located against the sintered electrode 51 of the electrolyte element so that a satisfactory electrical contact is established between the gauze pad and the electrolyte element. The periphery of the gauze pad as at 55, functions as a contact seat upon which a formed alloy wire 57 is mounted in such a manner as to establish electrical continuity between the gauze pad and the alloy wire. In the illustrated embodiment, the alloy wire 57 terminates at one end in a generally circular configuration which facilitates the mounting of the alloy wire 57 to the gauze pad through the use of multiple welds as at 59. The other end of the alloy wire is in communication with the sensor's measuring circuitry. The alloy wire 57, which as discussed above, consists preferably of either Chromel A or Inconel 600 alloy materials, is preferably 0.010 to 0.125 inch in diameter.

In FIG. 3, an alloy/platinum disc weld design utilizes an electrolyte element 31 having a sintered electrode 51 therein adapted to partially receive thereon a gauze pad 53. The periphery 55 of the gauze pad 53 extending out beyond the electrode 51 has a platinum disc 61 secured thereto in an electrically conductive relationship. The platinum disc 61 provides a mounting seat onto which the alloy wire 57 is welded as at 59.

Considering FIGS. 4A and 4B, an alloy-platinum extension lead lap joint design is illustrated. The electrolyte element 31 includes a sintered electrode 51 onto which a platinum gauze pad 53 is mounted. A platinum extension lead wire 63 is inserted into the platinum gauze-filled bore and welded into place. The alloy wire 65 has a semicircular cross section at at least one end thereof which forms a seat onto which a section of the platinum extension wire 63 is mounted by means of multiple welds as at 67.

In FIG. 5, an alloy-platinum extension lead butt joint design is illustrated. The electrolyte element 31 includes a sintered electrode 51 onto which a platinum gauze pad 53 is pressed. A platinum extension lead wire 63 is mounted onto the platinum gauze-covered electrode 51 and welded into place. The free end of the platinum lead wire is butt welded as at 69 to an alloy lead wire 71 to provide a single junction therebetween.

What has been described is a combination of materials and designs for electrode lead wires in gas measuring probes. These designs not only reduce the use of platinum, they also substantially eliminate much of the adverse unbalanced thermoelectric effect encountered in existing devices. Additionally, because the designs according to the present invention are welded rather than mechanical in nature, electrical continuity at the platinum-alloy interface remains substantially uneffected by surface oxidation. As a result, the present invention provides electrode lead configurations which can be used in gas analyzer probes in environments with temperatures in excess of 600° F.

I claim:
1. In a gas measuring probe having an ion-conductive solid electrolyte cell, a first portion of said cell being exposed to a flue gas stream and a second portion of said cell being exposed to a reference gas stream, and electrode lead means extending from said first and said second cell portions and in electrical communication with a remote measuring circuit the improvement where at least one of said electrode means comprises a platinum gauze pad; a sintered electrode disposed on said solid electrolyte cell and adapted to receive thereon at least a portion of said platinum gauze pad such that the periphery thereof extends from said sintered electrode and such that said platinum gauze pad is in electrical communication with said solid electrolyte cell; and an alloy wire having one end thereof welded to the periphery of said platinum gauze pad and the other end thereof in electrical communication with said measuring circuit.

2. The gas measuring probe of claim 1 wherein the alloy wire is selected from the group of alloys consisting of nickel-chromium-silicon and nickel-chromium-iron.

3. The gas measuring probe of claim 2 wherein the nickel-chromium-iron alloy comprises approximately 77 weight percent nickel, 15.8 weight percent chromium, and 7.2 weight percent iron.

4. The gas measuring probe of claim 2 wherein the nickel-chromium-silicon alloy comprises approximately 79 weight percent nickel, 20 weight percent chromium, and 1 weight percent silicon.

5. In a gas measuring probe having an ion-conductive solid electrolyte cell, a first portion of said cell being exposed to a flue gas stream and a second portion of said cell being exposed to a reference gas stream, and electrode lead means extending from said first and said second cell portions and in electrical communication with a remote measuring circuit the improvement where at least one of said electrode means comprises a platinum gauze pad; a sintered electrode disposed on said solid electrolyte cell and adapted to receive thereon at least a portion of said platinum gauze pad such that the periphery thereof extends from said sintered electrode and such that said platinum gauze pad is in electrical communication with said solid electrolyte cell; a platinum disc secured to and in electrical communication with said gauze pad; and an alloy wire having one end thereof welded to said platinum disc and the other end thereof in electrical communication with said measuring circuit.

6. The gas measuring probe of claim 5 wherein the alloy wire is selected from the group of alloys consisting of nickel-chromium-silicon and nickel-chromium-iron.

7. The gas measuring probe of claim 6 wherein the nickel-chromium-iron alloy comprises approximately 77 weight percent nickel, 15.8 weight percent chromium, and 7.2 weight percent iron.

8. The gas measuring probe of claim 6 wherein the nickel-chromium-silicon alloy comprises approximately 79 weight percent nickel, 20 weight percent chromium, and 1 weight percent silicon.

9. In a gas measuring probe having an ion-conductive solid electrolyte cell, a first portion of said cell being exposed to a flue gas stream and a second portion of said cell being exposed to a reference gas stream, and electrode lead means extending from said first and said second cell portions and in electrical communication with a remote measuring circuit the improvement where at least one of said electrode means comprises a platinum gauze pad; a sintered electrode disposed on said solid electrolyte cell and adapted to receive thereon at least a portion of said platinum gauze pad such that the periphery thereof extends from said sintered electrode and such that said platinum gauze pad is in electrical communication with said solid electrolyte cell; a platinum extension wire mounted in said gauze pad and extending therefrom; and an alloy lead wire of generally semicircular cross section defining thereby a seat portion, wherein said extending platinum lead wire is welded to said alloy wire seat portion.

10. The gas measuring probe of claim 9 wherein the alloy wire is selected from the group of alloys consisting of nickel-chromium-silicon and nickel-chromium-iron.

11. The gas measuring probe of claim 10 wherein the nickel-chromium-iron alloy comprises approximately 77 weight percent nickel, 15.8 weight percent chromium, and 7.2 weight percent iron.

12. The gas measuring probe of claim 10 wherein the nickel-chromium-silicon alloy comprises approximately 79 weight percent nickel, 20 weight percent chromium, and 1 weight percent silicon.

13. In a gas measuring probe having an ion-conductive solid electrolyte cell, a first portion of said cell being exposed to a flue gas stream and a second portion of said cell being exposed to a reference gas stream, and electrode lead means extending from said first and said second cell portions and in electrical communication with a remote measuring circuit the improvement where at least one of said electrode means comprises a platinum gauze pad; a sintered electrode disposed on solid electrolyte cell and adapted to receive thereon at least a portion of said platinum gauze pad such that the periphery thereof extends from said sintered electrode and such that said platinum gauze pad is in electrical communication with said solid electrolyte cell; a platinum extension wire mounted in said platinum gauze and extending therefrom; and an alloy lead wire butt welded in an end-to-end relationship with said platinum extension wire.

14. The gas measuring probe of claim 13 wherein the alloy wire is selected from the group of alloys consisting of nickel-chromium-silicon and nickel-chromium-iron.

15. The gas measuring probe of claim 14 wherein the nickel-chromium-iron alloy comprises approximately 77 weight percent nickel, 15.8 weight percent chromium, and 7.2 weight percent iron.

16. The gas measuring probe of claim 14 wherein the nickel-chromium-silicon alloy comprises approximately 79 weight percent nickel, 20 weight percent chromium, and 1 weight percent silicon.

* * * * *